United States Patent
Herzig

(10) Patent No.: US 8,115,025 B2
(45) Date of Patent: *Feb. 14, 2012

(54) METHOD FOR THE PRODUCTION OF β-KETOCARBONYL-FUNCTIONAL ORGANOSILICON COMPOUNDS

(75) Inventor: Christian Herzig, Waging (DE)

(73) Assignee: Wacker Chemie AG, Munich (DE)

( * ) Notice: Subject to any disclaimer, the term of this patent is extended or adjusted under 35 U.S.C. 154(b) by 146 days.

This patent is subject to a terminal disclaimer.

(21) Appl. No.: 12/599,187

(22) PCT Filed: May 19, 2008

(86) PCT No.: PCT/EP2008/056102
§ 371 (c)(1),
(2), (4) Date: Nov. 6, 2009

(87) PCT Pub. No.: WO2008/142041
PCT Pub. Date: Nov. 27, 2008

(65) Prior Publication Data
US 2010/0305348 A1    Dec. 2, 2010

(30) Foreign Application Priority Data

May 23, 2007 (DE) .......................... 10 2007 023 934

(51) Int. Cl.
*C07F 7/00* (2006.01)
(52) U.S. Cl. ........................................ 556/413; 556/425
(58) Field of Classification Search .................. 556/413, 556/425
See application file for complete search history.

(56) References Cited

U.S. PATENT DOCUMENTS

| | | |
|---|---|---|
| 4,808,649 A | 2/1989 | Gay et al. |
| 4,861,839 A | 8/1989 | Mizuguchi et al. |
| 5,952,443 A | 9/1999 | Wilt et al. |
| 6,121,404 A | 9/2000 | Liles |

*Primary Examiner* — Porfirio Nazario Gonzalez
(74) *Attorney, Agent, or Firm* — Brooks Kushman P.C.

(57) ABSTRACT

β-ketocarbonyl-functional organosilicon compounds are prepared by reacting an organosilicon compound containing at least one primary amino group with a compound which liberates a diketene, the reaction taking place in the presence of an organic compound which inhibits or prevents the reaction of diketenes with primary or secondary amino groups. The products are different from those produced merely by the reaction of a diketene with an amino-group-containing organosilicon compound.

10 Claims, No Drawings

METHOD FOR THE PRODUCTION OF β-KETOCARBONYL-FUNCTIONAL ORGANOSILICON COMPOUNDS

CROSS REFERENCE TO RELATED APPLICATION

This application is the U.S. national phase of PCT application No. PCT/EP2008/056102 filed May 19, 2008 which claims priority to German application DE 10 2007 023 934.5 filed May 23, 2007.

BACKGROUND OF THE INVENTION

1. Field of the Invention

The invention relates to a process for preparing β-ketocarbonyl-functional organosilicon compounds.

2. Description of the Related Art

U.S. Pat. No. 4,861,839 describes alkoxysilanes which are substituted by acetoacetic (thio)ester groups or acetoacetamido groups and are used as monomeric chelating ligands for metal catalysts.

Polymeric β-ketoestersiloxanes are known from U.S. Pat. No. 4,808,649, as is a process for preparing them and their use as stabilizer for polyvinyl chloride.

Functional polysiloxanes containing acetoacetate groups are described in U.S. Pat. No. 5,952,443, in which a portion of the functional groups must contain at least two β-ketocarbonyl groups per functional group and the number of dimethylsiloxy units is not greater than 50. Crosslinking by means of polyamines in surface coating formulations is also described.

The modification of carbinolsiloxanes or aminopoly-siloxanes by means of diketene and its derivatives is described in U.S. Pat. No. 6,121,404. The products are used in aqueous solution together with aminopolysiloxanes for producing elastomer films.

SUMMARY OF THE INVENTION

It was an object of the invention to provide a process for preparing β-ketocarbonyl-functional organosilicon compounds which gives ungelled products. This and other objects are achieved by the invention, whereby a diketene is reacted with aminoalkyl-functional organosilicon compounds, wherein at least one aminoalkyl group contains a primary amino group, the reaction taking place in the presence of the organic compound which retards or prevents reaction of primary or secondary amino groups with β-ketocarbonyl compounds.

The invention thus provides a process for preparing β-ketocarbonyl-functional organosilicon compounds using compounds (1) which eliminate diketenes of the general formula $$\underset{O}{\underset{|}{R^3-CH}}\underset{}{\overset{H}{\diagup}}\underset{}{\overset{R^3}{\diagdown}}=O, \tag{I}$$

where
$R^3$ is a hydrogen atom or a hydrocarbon radical having from 1 to 18 carbon atoms, preferably a hydrogen atom, which are reacted with organosilicon compounds (2) which contain at least one Si-bonded radical A of the general formula $$-R^1-NR^2{}_2 \tag{II}$$

per molecule, where $R^1$ is a divalent organic radical which has from 2 to 10 carbon atoms and may contain heteroatoms selected from the group consisting of oxygen, sulfur and nitrogen, preferably a hydrocarbon radical having from 2 to 10 carbon atoms, more preferably from 2 to 4 carbon atoms, $R^2$ is a hydrogen atom or an organic radical which has from 1 to 100 carbon atoms and may contain nitrogen atoms, preferably a hydrogen atom or an alkyl, cycloalkyl or aminoalkyl radical having from 1 to 30 carbon atoms, with the proviso that the radical of the formula (II) has at least one primary amino group and, if appropriate, at least one secondary amino group, preferably at least one primary amino group, in the presence of organic compounds (3) which retard or prevent the reaction of primary or secondary amino groups with β-ketocarbonyl compounds.

Preference is given to using compounds (1) which eliminate diketene of the formula $$CH_2=\underset{O}{\diagdown}\diagup=O$$

As compounds (1), it is possible to use diketene adducts with enolizable keto compounds, preferably the diketene-acetone adduct (2,2,6-trimethyl-4-oxo-1,3-dioxin or 2,2,6-trimethyl-4H-1,3-dioxin-4-one) of the formula

[structure of 2,2,6-trimethyl-4H-1,3-dioxin-4-one with CH₃ groups]

The compounds (1) are sufficiently stable under normal conditions but are subject to thermal decomposition, as a result of which diketene is set free again and is subsequently reacted with the organosilicon compounds (2).

As organosilicon compounds (2), it is possible to use silanes or oligomeric or polymeric organopolysiloxanes. The organosilicon compounds (2) preferably contain from 1 to 20,000 Si atoms, more preferably from 2 to 5000 Si atoms and most preferably from 60 to 3000 Si atoms. The organosilicon compounds (2) can be linear, branched, dendritic or cyclic and can also contain polymeric organic groups such as polyether, polyester or polyurea groups.

Preferably used as organosilicon compounds (2) are organopolysilozanes comprising units of the general formula $$A_a R_c (OR^4)_d SiO_{\frac{4-(a+c+d)}{2}} \tag{III}$$

where
A is a radical of the general formula —$R^1$—$NR^2{}_2$ (II), where $R^1$ and $R^2$ are as defined above, R is a monovalent, substituted or unsubstituted hydrocarbon radical having from 1 to 18 carbon atoms per radical,
$R^4$ is a hydrogen atom or an alkyl radical having from 1 to 8 carbon atoms, preferably a hydrogen atom or a methyl or ethyl radical,
a is 0 or 1,
c is 0, 1, 2 or 3 and
d is 0 or 1,
with the proviso that the sum a+c+d is 3 and on average at least one radical A is present per molecule.

Preferred examples of organosilicon compounds (2) are organopolysiloxanes of the general formulae $$A_g R_{2-g} SiO(SiR_2O)_l(SiRAO)_k SiR_{3-g}A_g \quad \text{(IVa)}$$

and $$(R^4O)R_2SiO(SiR_2O)_n(SiRAO)_m SiR_2(OR^4) \quad \text{(IVb)}$$

where A, R and $R^4$ are as defined above,
g is 0 or 1,
k is 0 or an integer from 1 to 30, preferably 0,
l is 0 or an integer from 1 to 1000, preferably 50 to 1000,
m is an integer from 1 to 30, preferably 1 to 5, and
n is 0 or an integer from 1 to 1000, preferably 50 to 500,
with the proviso that on average at least one radical A is present per molecule.

Further examples of organosilicon compounds (2) are organopolysiloxanes comprising units of the general formulae $$ASiO_{3/2} \quad \text{(Va)}$$

and $$R_e SiO_{\frac{4-e}{2}}, \quad \text{(Vb)}$$

organopolysiloxanes comprising units of the general formulae $$AR_2SiO_{1/2} \text{ and} \quad \text{(Vc)}$$

$$R_f SiO_{\frac{4-f}{2}}, \quad \text{(Vd)}$$

and organopolysiloxanes comprising units of the general formulae $$ARSiO \text{ and} \quad \text{(Ve)}$$

$$R_f SiO_{\frac{4-f}{2}}, \quad \text{(Vf)}$$

$$R_2SiO, \quad \text{(Vg)}$$

where A and R are as defined above,
e is 1, 2 or 3 and
f is 0 or 1.

The organosilicon compounds (2) used in the process of the invention preferably have a viscosity of from 1 mPa·s to 1,000,000 mPa·s at 25° C., preferably from 100 mPa·s to 100,000 mPa·s at 25° C.

Examples of radicals R are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals such as the cyclopentyl, cyclohexyl, cycloheptyl and methylcyclohexyl radicals; alkenyl radicals such as the vinyl, 5-hexenyl, cyclohexenyl, 1-propenyl, allyl, 3-butenyl and 4-pentenyl radicals; alkynyl radicals such as the ethynyl, propargyl and 1-propynyl radicals; aryl radicals such as the phenyl, naphthyl, anthryl and phenanthryl radicals; alkaryl radicals such as the o-, m-, and p-tolyl radicals, xylyl radicals and ethylphenyl radicals; and aralkyl radicals such as the benzyl radical, and the α- and β-phenylethyl radicals.

Examples of radicals $R^1$ are —$CH_2CH_2$—, —$CH(CH_3)$—, —$CH_2CH_2CH_2$—, —$CH_2C(CH_3)$ H—, —$CH_2CH_2CH_2CH_2$—, —$CH_2CH_2CH(CH_3)$—, with the —$CH_2CH_2CH_2$— radical being preferred.

Examples of hydrocarbon radicals R also apply to hydrocarbon radicals $R^2$. Further examples of $R^2$ are hydrogen and N-containing radicals such as
—$CH_2CH_2NH_2$, —$CH_2CH_2NHCH_3$, —$CH_2CH_2N(CH_3)_2$, —$CH_2CH_2CH_2NH_2$, $CH_2CH_2CH_2N(CH_3)_2$.

Examples of hydrocarbon radicals R also apply to hydrocarbon radicals $R^3$.

Examples of alkyl radicals $R^4$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical.

A preferred radical A is the radical of the general formula $$—R^1—NH—(CH_2)_2—NH_2 \quad \text{(VIa)}$$

or $$—R^1—NH_2 \quad \text{(VIa')},$$

where $R^1$ is as defined above, and a particularly preferred radical A is the radical of the formula $$—(CH_2)_3—NH—(CH_2)_2—NH_2 \quad \text{(VIb)}$$

or $$—(CH_2)_3—NH_2 \quad \text{(VIb')}.$$

As organic compounds (3), preference is given to using those which form more or less solid adducts with amines. It is possible to use one type of compound (3) or a plurality of types of compounds (3). Examples of compounds (3) are aldehydes and ketones. Preferred examples are acetone, butanone, methyl isobutyl ketone and cyclohexanone.

In the process of the invention, preference is given to firstly mixing the organosilicon compound (2) with the organic compound (3) and then adding the compound (1) which eliminates the diketene.

In the process of the invention, preference is given to reacting organosilicon compounds (2) with organic compounds (3), with the compounds (3) forming protective groups on the amino groups in the radical A of the formula (II), in a 1$^{st}$ stage and subsequently reacting the organosilicon compounds (2) having the protected amino groups (reaction products of (2) and (3)) obtained in the 1$^{st}$ stage with diketenes which are thermally eliminated from the compounds (1) in a 2$^{nd}$ stage.

In the reaction with diketene, the protective group is surprisingly split off from the amino group in the radical A of the formula (II) again.

If ketones are used as compounds (3), these react preferentially with the primary amino groups. This reaction is preferably carried out at from 0 to 90° C., more preferably from 10 to 60° C., i.e. the 1$^{st}$ stage of the process of the invention is preferably carried out at these temperatures.

The condensation reaction in the 1$^{st}$ stage leads to an equilibrium state which is far on the side of the reaction products of (2) and (3), so that only very few primary amino groups are still present.

Products formed by the condensation in the 1$^{st}$ stage are the reaction product of (2) and (3) and also water which is required later for regenerating free amino groups after addition of compound (1). It has been found that the few amino groups present in the equilibrium react with diketene from compound (1) to form β-ketoamides, whereupon an equilibrium is reestablished and small amounts of free amino groups are therefore continually formed. Secondary reactions are surprisingly avoided virtually entirely as a result of these low amine concentrations.

The water of condensation can be left in the mixture, be bound reversibly or be removed. If water is bound reversibly, it has to be set free again by means of suitable measures after introduction of diketene. In the case of physical absorption, this can usually be effected by heating. However, if water is removed from the reaction mixture, it has to be added again in at least the same amount after introduction of compound (1) so that the reaction of diketene set free from compound (1) with the amino groups can proceed to completion.

The water of condensation can be reversibly bound to absorbents which can take up water. Examples are zeolites and molecular sieves having pore sizes of 3 or even 4 Å. Water of condensation can also be bound as "water of crystallization" in inorganic salts such as sodium sulfate or magnesium sulfate used in anhydrous form. Reversibly bound water can be set free again by heating the reaction mixture to a suitable temperature and can thus be made available again for the regeneration of free primary or secondary amino groups.

Water of condensation can be removed completely from the reaction mixture if the absorbents are removed, e.g. by filtration, or these bind water so strongly that it can no longer be set free by methods which are compatible with the reaction. Permanent removal of water can also be effected by means of reduced pressure. In all these cases, renewed addition of water is necessary after the addition of compound (1). It can be introduced quickly, slowly or in portions.

The organic compounds (3) used in the process of the invention can remain in the product or else be removed, for example by distillation under reduced pressure or by extraction.

The organic compound (3) is preferably used in amounts of at least 1 mol, more preferably at least 1.5 mol, yet more preferably from 1 to 10 mol, and most preferably from 1.5 to 5 mol, per mole of amino group (primary and secondary) in the radical A of the general formula (II) in the organosilicon compound (2).

In the process of the invention, compounds (1) which eliminate diketene are preferably used in amounts of from 1.0 to 2.0 mol, more preferably from 1.0 to 1.7 mol, and most preferably from 1.0 to 1.5 mol, per mole of amino group (primary and secondary) in the radical A of the general formula (II) in the organosilicon compound (2).

A particular embodiment of the invention comprises the use of equimolar amounts of compounds (1) which eliminate diketene, and amino groups.

The process of the invention is preferably carried out at temperatures of from 80 to 180° C., more preferably from 120 to 160° C. In particular, the 2$^{nd}$ stage of the process of the invention is carried out at these temperatures. Furthermore, the process of the invention is preferably carried out at the pressure of the surrounding atmosphere, but can also be carried out at higher and lower pressures.

The β-ketocarbonyl-functional organosilicon compounds obtained by the process of the invention preferably contain at least one Si-bonded radical B containing a group of the general formula

—N(—Z)— (VII)

where
Z is a radical of the formula —C(=O)—CHR$^3$—C(=O)—CH$_2$R$^3$ per molecule.

The β-ketocarbonyl-functional organosilicon compounds obtained are preferably ones which contain, as Si-bonded radicals B, at least one radical of the general formula

or

where Z is as defined above and
x is 0 or 1,
per molecule, with the radical of the formula (IX) being particularly preferred.

A particularly preferred radical B is the radical of the formula

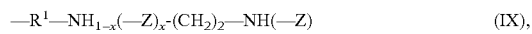

where Z is as defined above.

The invention therefore provides β-ketocarbonyl-functional organosilicon compounds which contain at least one Si-bonded radical of the general formula

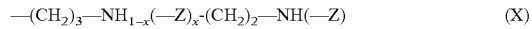

where Z is as defined above and
x is 0 or 1,
per molecule.

The β-ketocarbonyl-functional organosilicon compounds obtained are preferably organopolysiloxanes comprising units of the general formula

where B, R, R$^4$, a, c and d are as defined above, with the proviso that the sum of a+c+d is ≦3 and on average at least one radical B is present per molecule.

Preferred examples of β-ketocarbonyl-functional organosilicon compounds are organopolysiloxanes of the general formulae

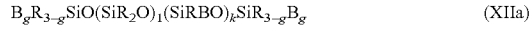

and

where B, R and R$^4$ are as defined above,
g is 0 or 1,
k is 0 or an integer from 1 to 30, preferably 0, and
l is 0 or an integer from 1 to 1000, preferably 50 to 1000,
m is an integer from 1 to 30, preferably 1 to 5, and
n is 0 or an integer from 1 to 1000, preferably 50 to 500, with the proviso that on average at least one radical B is present per molecule.

Further examples of β-ketocarbonyl-functional organosilicon compounds are organopolysiloxanes comprising units of the general formulae $(BSiO)_{3/2}$ and  (XIIIa)

$R_eSiO_{\frac{4-e}{2}}$,  (XIIIb)

organopolysiloxanes comprising units of the general formulae $BR_2SiO_{1/2}$ and  (XIVa)

$R_fSiO_{\frac{4-f}{2}}$,  (XIVb)

and organopolysiloxanes comprising units of the general formulae $BR_2SiO_{1/2}$ and  (XVa)

$R_fSiO_{\frac{4-f}{2}}$,  (XVb)

$R_2SiO$  (XVc)

where B, R, e and f are as defined above.

The β-ketocarbonyl-functional organosilicon compounds obtained by the process of the invention preferably have a viscosity of from 10 mPa·s to 10,000,000 mPa·s at 25° C., more preferably from 100 mPa·s to 500,000 mPa·s at 25° C.

The β-ketocarbonyl-functional organosilicon compounds of the invention can be used:
a) for fixing silicon compounds/siloxanes on surfaces containing amino groups, which can be controlled as a result of the pH dependence
b) for forming polymers (linear, branched) by means of reaction partners containing amino groups through to crosslinking, in which they function, depending on the functionality density, as crosslinkers or as polymers to be crosslinked
c) for fixing on substrates containing metal ions, in which case the metal ions bind to the products according to the invention with chelate formation and the bond strength depends on the type of ion,
d) for crosslinking by means of polyacrylates by Michael addition.

EXAMPLE 1

269 g of a dimethylpolysiloxane having 3-(aminoethylamino) propyl end groups and an amine content of 0.78 meq./g are mixed with 24.4 g of acetone at 22° C. After about 4 hours, the mixture is heated to reflux temperature and a total of 47.7 g of diketene-acetone adduct is introduced at a uniform rate and with good stirring. A slightly exothermic reaction occurs and the viscosity of the amine oil increases. The mixture is allowed to react further for another 2 hours under reflux and the acetone which has been added and which has been eliminated is removed at 70° C. under reduced pressure. Filtration through bentonite gives a clear oil having a viscosity of 1970 mm²/s (25° C.). The ¹H-NMR spectrum shows a keto/enol ratio of the β-ketoamido-siloxane formed of 4.7; the amine conversion is quantitative (>99%).

EXAMPLE 2

132.5 g of a commercial aminosiloxane composed of 3-(aminoethylamino)propylmethylsiloxy and dimethyl-siloxy units and methoxy end groups and having an amine content of 0.302 meq./g at a viscosity of 1130 mm²/s (25° C.) are stirred with 4.7 g of acetone at 25° C. for 4 hours. This is followed by heating to 120° C. and addition of 9.1 g of diketene-acetone adduct, resulting in a slight increase in temperature. After a further 2 hours, the acetone is removed at 70° C. under reduced pressure. Filtration through bentonite gives a clear oil having a viscosity of 5800 mm²/s (25° C.). The ¹H-NMR spectrum shows quantitative amine conversion. The β-ketoamidosiloxane has a keto/enol ratio of 3.7. Both the primary amino groups and the secondary amino groups have been acetoacylated.

Comparative Experiment in Accordance with U.S. Pat. No. 6,121,404:

Example 2 is carried out without addition of acetone, i.e. without compound (3), which has a conditioning effect on amino groups. The addition of diketene-acetone adduct likewise leads to an exothermic reaction, but the increase in viscosity is substantially greater. After a short time, the mixture becomes inhomogeneous. A partially gelled product which is only partly soluble in toluene is obtained. A viscosity can no longer be measured.

EXAMPLE 3

200 g of a linear polydimethylsiloxane having amino-propyl end groups in a concentration of 0.092 meq./g and a viscosity of 1220 mm²/s (25° C.) are stirred together with 4.3 g of acetone at 25° C. for 3 hours. After heating to 120° C., 4.2 g of diketene-acetone adduct are introduced. The mixture is allowed to react fully at the same temperature for a further 2 hours, after which the acetone is removed under reduced pressure. Filtration through bentonite gives a clear oil having a viscosity of 3040 mm²/s (25° C.) with complete conversion of the amine groups.

The invention claimed is:
1. A process for preparing β-ketocarbonyl-functional organosilicon compounds, comprising:
    in a first step, reacting at least one organosilicon compound which contains at least one Si-bonded radical A of the formula

$-R^1-NR^2_2$  (II)

per molecule, where
    $R^1$ is a divalent $C_{2-10}$ organic radical optionally containing one or more heteroatoms selected from the group consisting of oxygen, sulfur and nitrogen,
    $R^2$ is a hydrogen atom or a $C_{1-100}$ organic radical which optionally contain nitrogen atoms,
    with the proviso that the radical A of the formula (II) has at least one primary amino group and optionally one or more secondary amino groups,
    with at least one organic compound which retards or prevents the reaction of primary or secondary amino groups with β-carbonyl compounds,
    and in a second step,
        reacting a product obtained in the first step with at least one diketene precursor compound which eliminates diketenes of the formula

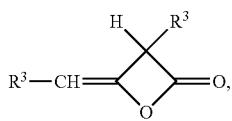

where
R³ is a hydrogen atom or a hydrocarbon radical having from 1 to 18 carbon atoms.

2. The process of claim 1, wherein a diketene-acetone adduct is used as a compound (1) which eliminates diketene.

3. The process of claim 1, wherein water liberated in a condensation in the 1$^{st}$ step is bound reversibly and set free again after addition of compound(s) which eliminate diketene.

4. The process of claim 1, wherein water liberated in a condensation in the 1$^{st}$ step is removed from the reaction mixture and is added again after addition of compound(s) which eliminate diketene.

5. The process of claim 1, wherein at least one aldehyde or ketone is used as the organic compound.

6. The process of claim 1, wherein at least one compound selected from the group consisting of acetone, butanone, methyl isobutyl ketone and cyclohexanone is used as the organic compound.

7. The process of claim 1, wherein the organic compound is used in amounts of at least 1 mol per mol of amino group (primary and secondary) in the radical A of the formula (II) in the organosilicon compound.

8. The process of claim 1, wherein the compounds which eliminate diketene are used in amounts of from 1.0 to 2.0 mol per mol of amino group (primary and secondary) in the radical A of the formula (II) in the organosilicon compound.

9. The process of claim 1, wherein the process is carried out at a temperature of from 80° C. to 180° C.

10. The process of claim 1, wherein the radical A is a radical of the formula

or

where
R¹ is a divalent $C_{2-10}$ organic radical optionally containing one or more heteroatoms selected from the group consisting of oxygen, sulfur and nitrogen.

* * * * *